US007994122B2

(12) United States Patent
Riber et al.

(10) Patent No.: US 7,994,122 B2
(45) Date of Patent: Aug. 9, 2011

(54) GLUCAGON ANALOGUES

(75) Inventors: Ditte Riber, Frederiksberg (DK); Eddi Meier, Værløse (DK); Trine Skovlund Ryge, Frederikssund (DK); Jens Rosengren Daugaard, Virum (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 12/664,534

(22) PCT Filed: Jun. 16, 2008

(86) PCT No.: PCT/GB2008/002041
§ 371 (c)(1),
(2), (4) Date: Apr. 19, 2010

(87) PCT Pub. No.: WO2008/152403
PCT Pub. Date: Dec. 18, 2008

(65) Prior Publication Data
US 2010/0204105 A1 Aug. 12, 2010

Related U.S. Application Data

(60) Provisional application No. 61/000,188, filed on Oct. 24, 2007.

(30) Foreign Application Priority Data

Jun. 15, 2007 (GB) .................................. 0711673.4
Aug. 15, 2007 (EP) .................................. 07016032

(51) Int. Cl.
*A61K 38/26* (2006.01)
(52) U.S. Cl. ....................................................... 514/7.2
(58) Field of Classification Search ........................ None
See application file for complete search history.

(56) References Cited

U.S. PATENT DOCUMENTS
2005/0070469 A1   3/2005   Bloom et al.

FOREIGN PATENT DOCUMENTS
| EP | 0082731 | 6/1983 |
|---|---|---|
| EP | 2025684 | 2/2009 |
| WO | WO 98/11125 | 3/1998 |
| WO | WO 99/25727 | 5/1999 |
| WO | WO 99/46283 | 9/1999 |
| WO | WO 01/04156 | 1/2001 |
| WO | WO 03/022304 | 3/2003 |
| WO | WO 2004/062685 | 7/2004 |
| WO | WO 2006/134340 | 12/2006 |
| WO | WO 2007/024899 | 3/2007 |
| WO | WO 2008/101017 | 8/2008 |

OTHER PUBLICATIONS

Authier et al., "Endosomal Proteolysis of Glucagon at Neutral pH Generates the Bioactive Degradation Product Miniglucagon-(19-29)," *Endocrinology* 144: 5353-5364, 2003.
Blache et al., "Endopeptidase from Rat Liver Membranes, Which Generates Miniglucagon from Glucagon," *J. Biol. Chem.* 268:21748-21753, 1993.
Cavanaugh et al., "Isolation and Structural Characterization of Proglucagon-Derived Peptides, Pancreatic Polypeptide, and Somatostatin from the Urodele *Amphiuma Tridactylum*," *Gen. Compar. Endocrin.* 101:12-20, 1996.
Dakin et al., "Oxyntomodulin Inhibits Food Intake in the Rat," *Endocrinology* 142:4244-4250, 2001.
England et al., "Glucagon Carboxyl-Terminal Derivatives: Preparation, Purification and Characterization," Biochem. 21:940-950, 1982.
Frandsen et al., "Glucagon: Structure-Function Relationships Investigated by Sequence Deletions," *Hoppe-Seyler's Z. Physiol. Chem.* 362:665-677, 1981.
Hjorth et al., "Glucagon and Glucagon-Like Peptide 1: Selective Receptor Recognition Via Distinct Peptide Epitopes," *J. Biol. Chem.* 269:30121-30124, 1994.
Joshi et al., "The Estimation of Glutaminyl Deamidation and Aspartyl Cleavage Rates in Glucagon," *Int J. Pharma.* 273:213-219, 2004.
Kallenbach et al., "Role of the Peptide Bond in Protein Structure and Folding," in *The Amide Linkage*, Chapter 18, pp. 599-619, 621, 622, 2000.
Zhu et al., "The Role of Dipeptidyl Peptidase IV in the Cleavage of Glucagon Family Peptides: In Vivo Metabolism of Pituitary Adenylate Cyclase Activating Polypeptide-(1-38)," *J. Biol. Chem.* 278:22418-22423, 2003.
NCBI Genbank Accession No. 721913A, downloaded Dec. 15, 2009.
Protest of U.S. Appl. No. 12/664,534 Pursuant to 37 C.F.R. § 1.291, mailed Jan. 13, 2010.
European Search Report from European Patent Application No. 07016032, completed Jan. 28, 2008.
International Search Report from PCT/GB2008/002041, completed Aug. 28, 2008, mailed Sep. 9, 2008.
International Preliminary Report on Patentability for PCT/GB2008/002041, issued Dec. 17, 2009.
Written Opinion of the International Searching Authority from PCT/GB2008/002041, completed Aug. 28, 2008, mailed Sep. 9, 2008.

*Primary Examiner* — Cecilia Tsang
*Assistant Examiner* — Thomas Heard
(74) *Attorney, Agent, or Firm* — Clark & Elbing LLP; Kristina Bieker-Brady

(57) ABSTRACT

The invention provides materials and methods for promoting weight loss or preventing weight gain in a subject. In particular, the invention provides novel glucagon analogue peptides effective in such methods and in the treatment of obesity, eating disorders, metabolic syndrome, and non-alcoholic liver steatosis. The peptides may mediate their effect by having increased selectivity for the GLP-1 receptor as compared to human glucagon.

8 Claims, 2 Drawing Sheets

SEQUENCE LISTING

```
<160> NUMBER OF SEQ ID NOS: 6

<210> SEQ ID NO 1
<211> LENGTH: 39
<212> TYPE: PRT
<213> ORGANISM: Artificial sequence
<220> FEATURE:
<223> OTHER INFORMATION: Synthetic sequence: Exendin-4 amide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 37
<212> TYPE: PRT
<213> ORGANISM: Homo sapiens

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30
```

```
Arg Asn Asn Ile Ala
        35

<210> SEQ ID NO 3
<211> LENGTH: 29
<212> TYPE: PRT
<213> ORGANISM: Artificial sequence
<220> FEATURE:
<223> OTHER INFORMATION: Synthetic sequence: Glucagon analogue peptide

<400> SEQUENCE: 3

His Ser Gln Gly Thr Phe Thr Ser Asp Tyr Ser Lys Tyr Leu Asp Arg
1               5                   10                  15

Ala Arg Ala Asp Asp Phe Val Ala Trp Leu Lys Ser Thr
            20                  25

<210> SEQ ID NO 4
<211> LENGTH: 29
<212> TYPE: PRT
<213> ORGANISM: Homo sapiens

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 5
<211> LENGTH: 8
<212> TYPE: PRT
<213> ORGANISM: Homo sapiens

<400> SEQUENCE: 5

Lys Arg Asn Arg Asn Asn Ile Ala
1               5

<210> SEQ ID NO 6
<211> LENGTH: 69
<212> TYPE: PRT
<213> ORGANISM: Artificial sequence
<220> FEATURE:
<223> OTHER INFORMATION: Synthetic sequence: Glucagon analogue peptide
<220> FEATURE:
<221> NAME/KEY: VARIANT
<222> LOCATION: (1)..(20)
<223> OTHER INFORMATION: May be present or absent. If present,
      represents a peptide sequence of 1 - 20 amino acids wherein each
      Xaa may be absent or is selected from the group consisting of Ala,
      Leu, Ser, Thr, Tyr, Asn, Gln, Asp, Glu, Lys, Arg, His, Met, Har,
      Dbu, Dpr & Orn
<220> FEATURE:
<221> NAME/KEY: VARIANT
<222> LOCATION: (50)..(69)
<223> OTHER INFORMATION: May be present or absent. If present,
      represents a peptide sequence of 1 - 20 amino acids wherein each
      Xaa may be absent or is selected from the group consisting of
      Ala, Leu, Ser, Thr, Tyr, Asn, Gln, Asp, Glu, Lys, Arg, His, Met,
      Har, Dbu, Dpr & Orn

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa His Ser Gln Gly Thr Phe Thr Ser Asp Tyr Ser Lys
            20                  25                  30

Tyr Leu Asp Arg Ala Arg Ala Asp Asp Phe Val Ala Trp Leu Lys Ser
                35                  40                  45
```

```
Thr Xaa Xaa Xaa Xaa Xaa Xaa Xaa Xaa Xaa Xaa Xaa Xaa Xaa Xaa
    50              55                  60

Xaa Xaa Xaa Xaa Xaa
65
```

GLUCAGON ANALOGUES

CROSS-REFERENCE TO RELATED APPLICATIONS

This application is the national stage of International Application No. PCT/GB2008/002041, filed Jun. 16, 2008, which claims the benefit of U.S. Provisional Application No. 61/000,188, filed Oct. 24, 2007, European Application No. 07016032.0, filed on Aug. 15, 2007, and Great Britain Application No. 0711673.4, filed on Jun. 15, 2007.

Incorporation by Reference of a Sequence Listing Filed Electronically

The .txt file Sequence Listing concurrently filed with this application electronically having the name 50412.056002_ST25.txt, file size 3.401 kB, created on Dec. 14, 2009, is incorporated by reference.

FIELD OF THE INVENTION

The present invention relates to glucagon analogues and their medical use, for example in the treatment of excess food intake, obesity and excess weight.

BACKGROUND OF THE INVENTION

Treatment of obese patients with the peptide oxyntomodulin (Oxm) has been shown effective in obtaining weight loss, and several attempts have been made to obtain a useful medicament based on the native human oxyntomodulin sequence or modifications thereof [see, for example, WO03/022304 and WO2004/062685]. Oxyntomodulin is known to activate both the GLP-1 (glucagon-like peptide 1) receptor and the glucagon receptor, and it has been suggested that the GLP-1 receptor is essential for the anorectic function of Oxm.

Oxyntomodulin is derived from proglucagon, which is a 158 amino acid peptide processed differently in different organs. Whereas glucagon (29 amino acids in length; His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr) is produced in the pancreas, the longer 37 amino acid peptide oxyntomodulin (His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala) is produced in the intestine and brain. Oxyntomodulin consists of the full length glucagon and a C-terminal octapeptide (termed "intervening peptide 1" or IP-1, sequence Lys-Arg-Asn-Arg-Asn-Asn-Ile-Ala). Both glucagon and IP-1 fail to affect food intake when administered separately (Dakin, C. L. et al. (2001), Endocrin. 142, 4244-4250).

Both peptides are a substrate for the endogenous enzyme dipeptidyl peptidase which cleaves at the C-terminal side of Ser2 (Zhu, L. et al. (2003), J. Biol. Chem. 278, 22418-22423). Moreover it is found that a proteolytic fragment of glucagon is liberated following cleavage of glucagon at the Arg17-Arg18 amino acid doublet (Blache, P. at al. (1993) J. Biol. Chem. 268, 21748-21753).

SUMMARY OF THE INVENTION

Without wishing to be bound by any particular theory, the present inventors believe that the anorectic effects of Oxm can be mimicked by analogues of glucagon which have an increased selectivity for the GLP-1 receptor. This enables a peptide to be used which has pharmacological effects similar to oxyntomodulin, but potentially has a shorter primary peptide chain like that of glucagon to facilitate production through solid phase peptide synthesis.

It is also believed that glucagon agonist activity may also be required for the anorectic effect to be demonstrated.

The invention provides a glucagon analogue peptide of the formula:

wherein:
$R^1$ is hydrogen, $C_{1-4}$ alkyl (e.g. methyl), acetyl, formyl, benzoyl or trifluoroacetyl;
$R^2$ is $NH_2$ or OH;
$Z^1$ and $Z^2$ are independently absent or a peptide sequence of 1-20 amino acid units selected from the group consisting of Ala, Leu, Ser, Thr, Tyr, Asn, Gln, Asp, Glu, Lys, Arg, His, Met, Har, Dbu, Dpr and Orn;
or a pharmaceutically acceptable salt or derivative thereof.

The invention further provides a method of promoting weight loss or preventing weight gain in a subject, comprising administering said glucagon analogue peptide to the subject. In some embodiments, the invention provides use of the peptide for the treatment of obesity, eating disorders, metabolic syndrome, and non-alcoholic liver steatosis.

Also provided is the use of said glucagon analogue peptide in the preparation of a medicament for promoting weight loss or preventing weight gain in a subject.

The methods and uses of the invention also extend to nucleic acids encoding the glucagon analogue peptide, expression vectors comprising such nucleic acids, and host cells containing such nucleic acids or expression vectors.

Also provided is the glucagon analogue peptide, nucleic acid, expression vector or host cell as described, for use in a method of promoting weight loss or preventing weight gain in a subject.

Also provided is the glucagon analogue peptide, nucleic acid, expression vector or host cell as described, for use in a method of medical treatment.

The glucagon analogue peptide may have higher GLP-1 receptor selectivity than human glucagon. Typically it also has glucagon agonist activity, i.e. it is a GLP-1/glucagon co-agonist.

The GLP-1 or glucagon agonist activity of any given glucagon analogue peptide may be quantified by determining an EC50 value for that peptide in a selected assay for GLP-1 or glucagon activity. As the skilled person will be well aware, the EC50 value is a measure of the concentration at which half of that compound's maximal activity in the particular assay is achieved. In this specification, the EC50 value in an assay for GLP-1 or glucagon agonist activity will be referred to as EC50[GLP-1] and EC50[Glu] respectively. Where EC50 values for different compounds are compared, it will be understood that they describe the activity of the relevant compounds in the same assay under otherwise identical conditions.

The ratio EC50[Glu]/EC50[GLP-1] for the glucagon analogue peptide may be greater than the ratio EC50[Glu]/EC50[GLP-1] for glucagon. This may be interpreted to mean that the glucagon analogue peptide has a greater selectivity for GLP-1 receptor than glucagon.

The glucagon analogue peptide may have the formula:

or a pharmaceutically acceptable salt or derivative thereof;

The invention further provides a nucleic acid encoding the glucagon analogue peptide of the invention, an expression vector comprising such a nucleic acid, and a host cell containing such a nucleic acid or expression vector.

As well as providing a glucagon analogue that may have improved chemical stability and biological activity, the present invention also relates to providing compounds that have anti-obesity and/or feeding reducing activity in a mammal or human being in need of treatment.

Without wishing to be bound by theory, it is believed that the substitution at position 27 may improve oxidative stability relative to human glucagon. Similarly, the substitutions at positions 20, 24 and 28 may increase stability against deamidation relative to human glucagon. The glucagon analogue of the invention may therefore exhibit enhanced stability towards deamidation, and/or towards oxidative degradation, relative to the wild type glucagon. Further the peptide of this invention may exhibit enhanced stability towards in vivo degradation, perhaps due to the substitutions in the twin arginine site at position 17-18 of human glucagon.

In a further aspect, the present invention provides a composition comprising a glucagon analogue peptide as defined herein, or a salt or derivative thereof, a nucleic acid encoding such a glucagon analogue peptide, an expression vector comprising such a nucleic acid, or a host cell containing such a nucleic acid or expression vector, in admixture with a carrier. In preferred embodiments, the composition is a pharmaceutically acceptable composition and the carrier is a pharmaceutically acceptable carrier. The glucagon peptide analogue may be a pharmaceutically acceptable acid addition salt of the glucagon analogue.

The glucagon analogue peptides described find use in preventing weight gain or promoting weight loss. By "preventing" is meant inhibiting or reducing weight gain when compared to the absence of treatment, and is not necessarily meant to imply complete cessation of weight gain. Thus the peptides can be used for direct or indirect therapy of any condition caused or characterised by excess body weight, such as the treatment and/or prevention of obesity, and/or prevention of morbid obesity and metabolic syndrome, which is characterized by hypertriglyceridemia, low HDL-cholesterol, elevated apolipoprotein B, small dense LDL particles, inflammatory profile, insulin resistance, hyperinsulinemia, glucose intolerance, impaired fibrinolysis as well as endothelial and mitochondrial dysfunction. Metabolic syndrome is highly associated with increased prevalence of type-2 diabetes, hypertension, arteriosclerosis and coronary heart diseases. The peptides may cause a decrease in food intake and/or increased energy expenditure, resulting in the observed effect on body weight.

As already described, the invention extends to expression vectors comprising the above-described nucleic acid sequence, optionally in combination with sequences to direct its expression, and host cells transformed with the expression vectors. Preferably the host cells are capable of expressing and secreting the glucagon analogue. In a still further aspect, the present invention provides a method of producing the glucagon analogue, the method comprising culturing the host cells under conditions suitable for expressing the glucagon analogue and purifying the glucagon analogue thus produced.

The invention further provides a nucleic acid of the invention, an expression vector of the invention, or a host cell capable of expressing and secreting a glucagon analogue of the invention, for use in therapy. It will be understood that the nucleic acid, expression vector and host cells may be used for treatment of any of the disorders described herein which may be treated with the glucagon analogues themselves. References to a therapeutic composition comprising a glucagon analogue of the invention, or administration of a glucagon analogue of the invention, should therefore be construed to encompass administration of a nucleic acid, expression vector or host cell of the invention except where the context demands otherwise.

DETAILED DESCRIPTION OF THE INVENTION

Figure 1:
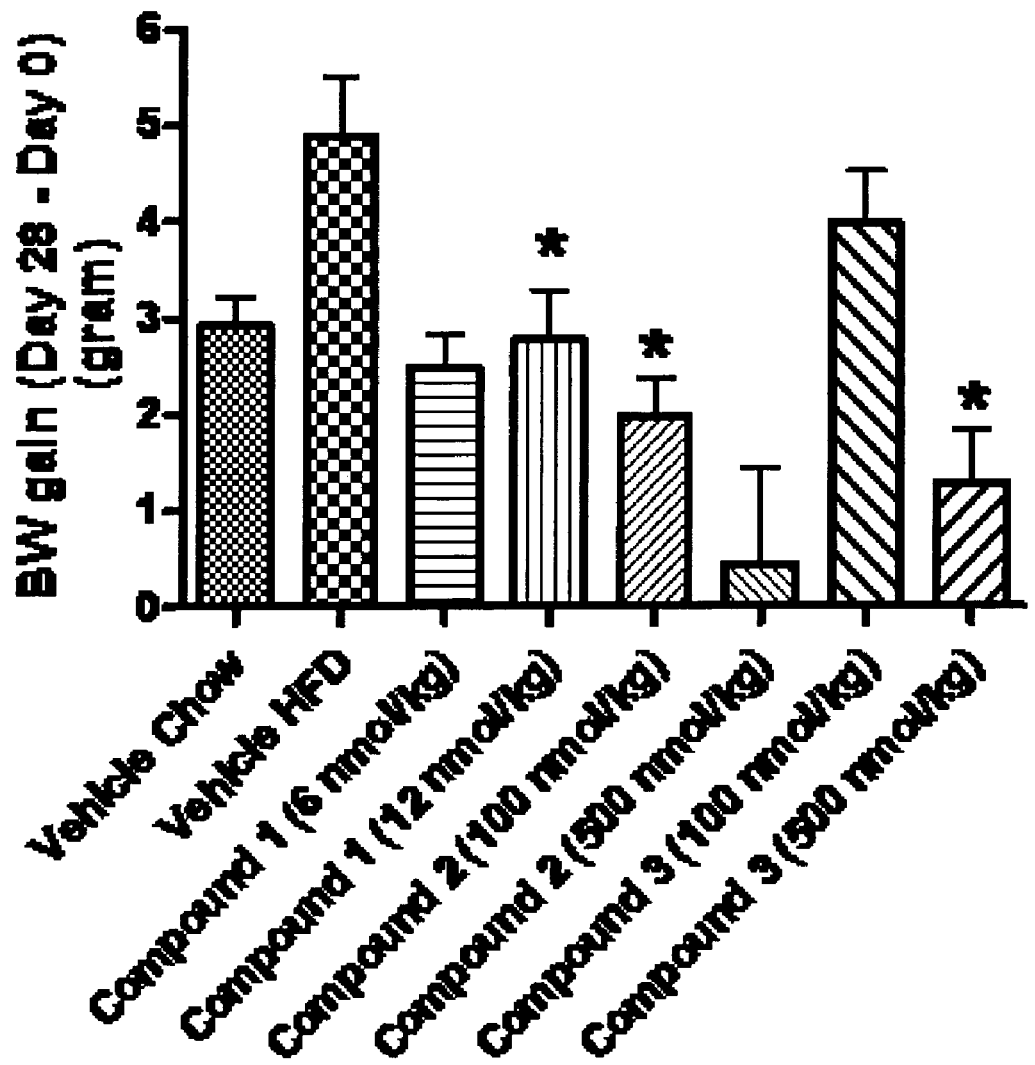
FIG. 1 shows body weight gain in high fat fed/high fat diet (HFD)(DIO) mice treated s.c. with vehicle, Exendin-4 amide (1-39) or Compound 1 (H-HGEGTFTSDLSKQMEEEAVR-LFIEWLKNGGPSSGAPPPS-NH$_2$), (SEQ ID No 1) oxyntomodulin or Compound 2 (H-HSQGTFTSDYSKYLDSR-RAQDFVQWLMNTKRNRNNIA-OH) (SEQ ID No 2) and the peptide (or Compound 3 (H-HSQGTFTSDYSKY-LDRARADDFVAWLKST-NH$_2$) (SEQ ID No 3) for 28 days. Animals eating chow are also included for comparison.

Throughout the description and claims the conventional one-letter and three-letter codes for natural amino acids are used as well as generally accepted three letter codes for other α-amino acids, such as sarcosin (Sar), norleucine (Nle) and α-aminoisobutyric acid (Aib). All amino acid residues in peptides of the invention are preferably of the L-configuration. However, D-configuration amino acids may also be present.

It should be understood that the peptides of the invention might also be provided in the form of a salt or other derivative. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$ where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

Other derivatives of the glucagon analogues of the invention include coordination complexes with metal ions such as $Mn^{2+}$ and $Zn^{2+}$, esters such as in vivo hydrolysable esters, free acids or bases, hydrates, prodrugs or lipids. Esters can be formed between hydroxyl or carboxylic acid groups present in the compound and an appropriate carboxylic acid or alcohol reaction partner, using techniques well known in the art. Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. Examples of prodrugs include the use of protecting groups which may be removed in situ releasing active compound or serve to inhibit clearance of the drug in vivo.

The analogue may comprise an additional N- or C-terminal peptide sequence of 3-20 amino acids, for example to stabilise the conformation and/or secondary structure of the glucagon analogue peptide, and/or to make the glucagon analogue peptide more resistant to enzymatic hydrolysis, e.g. as described in WO99/46283. These additional N- and C-terminal peptide sequences are designated $Z^1$ and $Z^2$ respectively.

When present, $Z^1$ and $Z^2$ each independently represent a peptide sequence of 3-20 or 4-20 amino acid residues, e.g. in the range of 4-15, more preferably in the range of 4-10 in particular in the range of 4-7 amino acid residues, e.g., of 4, 5, 6 or 7 amino acid residues, such as 6 amino acid residues. Each of the amino acid residues in the peptide sequences Z may independently be selected from Ala, Leu, Ser, Thr, Tyr, Asn, Gln, Asp, Glu, Lys, Arg, His, Met, Orn. Preferably, the amino acid residues are selected from Ser, Thr, Tyr, Asn, Gln, Asp, Glu, Lys, Arg, His, Orn, and Met, as well as amino acids falling within formula I as defined in WO01/04156, e.g., Dbu (2,4 diaminobutyric acid) or Dpr (2,3-diaminopropanoic acid), and more preferably may be selected exclusively from Glu, Lys, and Met, especially Lys. The above-mentioned amino acids may have either D- or L-configuration, but preferably the above-mentioned amino acids have an L-configuration. Particularly preferred sequences Z are sequences of four, five, six or seven consecutive lysine residues (i.e. $Lys_3$, $Lys_4$, $Lys_5$, $Lys_6$ or $Lys_7$), and particularly five or six consecutive lysine residues. Exemplary sequences Z are shown in WO 01/04156.

In certain preferred embodiments, $Z^1$ is absent. In such cases, $Z^2$ may be either present or absent. When $Z^1$ is present $R^1$ may be H, and when $Z^2$ is present $R^2$ may be OH.

When present at the C-terminus ($Z^2$), this additional peptide sequence typically has no more than 25% sequence identity with the corresponding sequence of the IP-1 portion of OXM (which has the sequence Lys-Arg-Asn-Arg-Asn-Asn-Ile-Ala).

"Percent (%) amino acid sequence identity" with respect to the another polypeptide sequence (e.g. glucagon, Oxm or IP-1) is calculated as the percentage of amino acid residues in a glucagon analogue peptide sequence that are identical with corresponding amino acid residues in the corresponding sequence of that other polypeptide when the two are aligned with one another, introducing gaps for optimal alignment if necessary.

When $Z^1$ is present $R^1$ may be H, and when $Z^2$ is present $R^2$ may be OH.

Agonist Activity and Receptor Selectivity

The glucagon analogue peptides described in this specification may have higher GLP-1 receptor selectivity than human glucagon. In some embodiments, they may also have higher GLP-1 agonist activity than human glucagon.

Binding of the relevant compounds to GLP-1 or glucagon receptors may be used as an indication of agonist activity, but in general it is preferred to use a biological assay which measures intracellular signalling caused by binding of the compound to the relevant receptor. For example, production of cyclic AMP (cAMP) is often used to monitor both GLP-1 and glucagon receptor activity, and hence can be used to determine glucagon analogue peptide agonist activity towards each type of receptor.

The skilled person will be aware of suitable assay formats, and examples are provided below. The GLP-1 receptor and/or the glucagon receptor may have the sequence of the receptors as described in the examples. E.g., the assays may make use the human glucagon receptor (Glucagon-R) having primary accession number P47871 (GI 1346144) and/or the human glucagon-like peptide 1 receptor (GLP-1R) having primary accession number P43220 (GI 1169956). (Where sequences of precursor proteins are referred to, it should of course be understood that assays may make use of the mature protein, lacking the signal sequence).

EC50 values may be used as a numerical measure of agonist activity. An EC50 value is a measure of the concentration of a compound required to achieve half of that compound's maximal activity in a particular assay. Thus a compound having EC50[GLP-1] lower than the EC50[GLP-1] of glucagon in a particular assay may be considered to have a higher GLP-1 agonist activity than glucagon.

By "higher selectivity" for GLP-1 is meant that the ratio of the compound's GLP-1 agonist activity to its glucagon agonist activity is higher than that of glucagon. That is to say, for a particular level of glucagon agonist activity, the analogue will display a higher level of GLP-1 agonist activity than glucagon. Since the EC50 values are inversely related to activity, this means that the ratio EC50[Glu]/EC50[GLP-1] for the glucagon analogue peptide may be greater than the ratio EC50[Glu]/EC50[GLP-1] for glucagon.

It may in some embodiments be preferred that the glucogon analogue has a higher GLP-1 agonist activity than human glucagon. (Accordingly, it may have a lower EC50 [GLP-1] than the EC50[GLP-1] for human glucagon.)

However, in other embodiments, the GLP-1 agonist activity may be substantially similar to, or lower than, human glucagon, provided that the ratio of GLP-1/glucagon agonist activity remains higher for the analogue than for human glucagon (i.e., the glucagon agonist activity is correspondingly reduced).

As mentioned above, typically the glucagon analogue peptide also has glucagon agonist activity, i.e. it is a GLP-1/glucagon co-agonist.

The glucagon analogue peptide may have substantially similar glucagon agonist activity to human glucagon (indeed, it may have a higher activity provided that the GLP-1 agonist activity is correspondingly increased). However the glucagon agonist activity may also be lower than that of human glucagon, as long as it is sufficient for anorectic activity.

Stability Studies

The skilled person will be able to design appropriate methods (e.g. quantitative methods) for detection of degradation products of glucagon analogues, e.g. based on those described below. Degradation may occur as oxidation, hydrolysis and deamidation, depending on the identity and position of the amino acids in any given glucagon analogue, and conditions as pH, solution and temperature. The compounds can be ranked according to chemical stability, when the compounds are incubated under stressed conditions (i.e. conditions likely to cause degradation) and subsequently analysed for content of remaining intact peptide. In addition, the knowledge gained about major degradation products obtained under stressed conditions will be important for any later analytical method development.

Quantitative Assays to Detect Glucagon Analogues

The skilled person will also be capable of designing methods (e.g. quantitative methods) for detection of glucagon analogues in complex environments or solutions (e.g. plasma, urine, tissue homogenates, cell homogenates, saliva or similar) to investigate the absorption, distribution, metabolism and excretion of the glucagon analogues after administration to mammals or as part of functional studies of in vitro cell systems.

In one embodiment, a quantitative assay can be based on antibodies raised against the glucagon analogues or fragments thereof. The antibodies obtained from the immunized animals can be used for quantitative assays. In one example a direct sandwich ELISA can be prepared using a first antibody with affinity of one part of the molecule immobilized in a multi-well plate. The sample is then applied to the wells and the glucagon analogue is captured by the first antibody. The captured glucagon analogue is then recognized by a second antibody with affinity for another part of the glucagon analogue. The second antibody can be labeled with an enzyme (horseradish peroxidase, alkaline phosphatase or beta-galactosidase) or a radioisotope. The amount of captured glucagon analogue can then be detected by addition of a colorimetric substrate or direct counting of radio-emission or by scintillation. Alternatively, the amount of captured glucagon analogue can be detected indirectly by addition of a labeled antibody with affinity for the second antibody. The concentration in the sample can be estimated from the response obtained from an external standard curve containing known amounts of glucagon analogue. Alternatively, the antibodies can be used to prepare a direct competitive immuno assay, where an antibody specific for the glucagon analogue is immobilized on a multi-well plate and the sample incubated in the wells with a predefined fixed concentration of labeled glucagon analogue. The label can be an enzyme, a fluorophore, a radioisotope or biotin and detected using, for example, substrates (e.g. colorimetric, fluorometric or chemiluminiscent) specific for the enzymes, scintillation or avidin linked to an enzyme followed by detection as described above. The amount of bound labeled glucagon analogue can be detected by an appropriate method and the concentration of glucagon analogue present in the sample derived from the response obtained from an external standard curve as described above.

In another embodiment, a quantitative assay can be based on liquid chromatography tandem mass spectroscopy methodology. In such a set up, the response from a fragment specific for the glucagon analogue to be studied is monitored upon fragmentation of the parent compound induced by collision with an inert gas (He or Ar). Prior to fragmentation the sample components can be separated by reversed phase chromatography or the sample can be injected directly in the mass spectrometer. If suitable the sample can be subjected to pretreatment (i.e., addition of protease inhibitors, protein precipitation, solid phase extraction, immuno-affinity extraction, etc). The concentration of glucagon analogue present in the sample derived from the response obtained from an external standard curve as described above, potentially after correction of the response using an internal standard similar to the glucagon analogue to be studied.

Generation of Specific Antibodies

Specific antibodies against the glucagon analogues or fragments thereof can be induced in mammals and purified from the serum. The glucagon analogues or fragments can either be used directly with an adjuvant to immunize rabbits, mice or other mammals, or the glucagon analogues or fragments thereof can be chemically linked to a carrier molecule (i.e., keyhole limpet hemocyanin, ovalbumin, albumin etc.) and injected with an adjuvant. The injections can be repeated with 2-4 weeks intervals for extended periods to improve the affinity and selectivity of the antibodies. Polyclonal antibodies can be harvested directly from the serum. To obtain monoclonal antibodies, B cells isolated from immunized animals, preferably mice, should be fused with tumor cells to form antibody producing hybridomas. Screening and selection of the appropriate clones and antibodies can be performed using either immobilized glucagon analogues or peptides thereof followed by detection with labeled anti-antibodies. Alternatively the screening and selection could be based on immobilized antibodies followed by detection with labeled glucagon analogues or fragments thereof. In all cases, the label could be a radioisotope, an enzyme, a fluorophore or biotin and detected using, for example, substrates (e.g. colorimetric, fluorometric or chemiluminescent) specific for the enzymes, scintillation or avidin linked to an enzyme followed by detection as described.

Synthesis of Glucagon Analogues

It is preferred to synthesize the analogues of the invention by means of solid phase or liquid phase peptide synthesis. In this context, reference is given to WO 98/11125 and, amongst many others, Fields, G B et al., 2002, "Principles and practice of solid-phase peptide synthesis". In: Synthetic Peptides (2nd Edition) and the Examples herein.

Thus the glucagon analogues may be synthesized in a number of ways including for example, a method which comprises:

(a) synthesizing the peptide by means of solid phase or liquid phase peptide synthesis and recovering the synthetic peptide thus obtained; or (b) expressing a nucleic acid construct that encodes the peptide in a host cell and recovering the expression product from the host cell culture; or (c) effecting cell-free in vitro expression of a nucleic acid construct that encodes the peptide and recovering the expression product; or a combination of methods of (a), (b), and (c) to obtain fragments of the peptide, subsequently ligating the fragments to obtain the peptide, and recovering the peptide.

Thus, it may be advantageous to exploit genetic engineering techniques. This may be the case when the peptide is sufficiently large (or produced as a fusion construct) and when the peptide only includes naturally occurring amino acids that can be translated from RNA in living organisms.

For the purpose of recombinant gene technology nucleic acid fragments encoding the peptides of the invention are important chemical products. Hence, a further aspect of the present invention provides a nucleic acid molecule comprising a nucleic acid sequence encoding a glucagon analogue of the invention, where the peptide preferably is comprised by naturally occurring amino acids. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details of the construction of these vectors of the invention will be familiar to the skilled person and construction of such vectors will be well within the skilled person's ability.

When producing the peptide of the invention by means of transformed cells, it is convenient, although far from essential, that the expression product is either exported (secreted) out into the culture medium or carried on the surface of the transformed cell.

Alternatively, peptides be prepared in vitro in cell free systems. This is especially expedient in cases where the peptides could be toxic for putative host cells. Thus, the present invention also contemplates use of cell-free in vitro translation/expression in order to prepare the peptides of the invention. In this context, reference is made to commercially available in vitro translation kits, materials, and technical documentation from e.g. Ambion Inc., 2130 Woodward, Austin, Tex. 78744-1832, USA.

Finally, the available methods can of course be combined so as to prepare e.g. semi-synthetic analogues. In such a set up, peptide fragments are prepared using at least 2 separate steps or methods, followed by ligation of the fragments to obtain the final peptide product.

Pharmaceutical Compositions and Administration

The glucagon analogues of the present invention, or salts or derivatives thereof, may be formulated as pharmaceutical compositions prepared for storage or administration, and which comprise a therapeutically effective amount of a glucagon peptide of the present invention, or a salt or derivative thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, but will depend on such factors as weight, diet, concurrent medication and other factors, well known those skilled in the medical arts.

It is within the invention to provide a pharmaceutical composition, wherein the glucagon analogue, or a salt thereof is present in an amount effective in adjunctive therapy to improve glycemic control and induce prolonged weight loss in people with obesity and type II diabetes (e.g. treated with antidiabetics such as metformin, a sulfonylurea, a glinide, a DPP-IV inhibitor, a glitazone, insulin or a combination of antidiabetics) who have not achieved adequate glycemic control.

Furthermore, it is within the invention to provide a pharmaceutical composition wherein the glucagon analogue, or a salt thereof is administered in combination with one or more other anti-obesity agents such as Neuropeptide Y (NPY), Agouti-related protein (AGRP), Melanin concentrating hormone (MCH), Hypocretins/Orexins, Ghrelin, Galanin, Growth Hormone-releasing Hormone (GHRH), Dynorphin, Beta-Endorphin, Beacon, 26RFa, Adiponectin, POMC, CART, Neurotensin (NT), Cholecystokinin (CCK), Corticotropin-releasing Hormone (CRH), Urocortin, Tyrotropin-releasing Hormone (TRH), Glucagon-like Peptide-1 (GLP-1), Galanin-like Peptide (GALP), PYY(3-36), Leptin, Neuropeptide K (NPK), Calcitonin-gene Related Peptide (CGRP), Prolactin-releasing Peptide (PrRP), Neuromedin B, Neuromedin U, Neuropeptide B (NPB), NPW, Somastostatin, Oxytocin, Bombesin, Motilin, Enterostatin, Amylin, Oxyntomodulin, Bombinakinin B or Alpha-MSH.

Pharmaceutically acceptable salts of the compound of the invention having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine; pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also may be formed. Similarly, when a compound of the present invention contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, and camphorsulfonic as well as other known pharmaceutically acceptable acids. Amino acid addition salts can also be formed with amino acids such as lysine, glycine, or phenylalanine.

As is apparent to one skilled in the medical art, a "therapeutically effective amount" of the peptide or pharmaceutical compositions of the present invention will vary depending upon the age, weight and mammalian species treated, the particular mode of administration and the desired effects and the therapeutic indication. Because these factors and their relationship to determining this amount are well known in the medical arts, the determination of therapeutically effective dosage levels, the amount necessary to achieve the desired result of preventing and/or treating excess body weight or obesity, including morbid obesity, metabolic syndrome, type-2 diabetes, hypertension, atherosclerois, arteriosclerosis and coronary heart diseases, as well as other medical indications disclosed herein, will be within the ambit of the skilled person.

As used herein, "a therapeutically effective amount" is one which reduces symptoms of a given condition or pathology, and preferably which normalizes physiological responses in an individual with the condition or pathology. Reduction of symptoms or normalization of physiological responses can be determined using methods routine in the art and may vary with a given condition or pathology. In one aspect, a therapeutically effective amount of a glucagon analogue or pharmaceutical composition analogue is an amount which restores a measurable physiological parameter to substantially the same value (preferably to within +30%, more preferably to within +20%, and still more preferably, to within 10% of the value) of the parameter in an individual without the condition or pathology.

In one embodiment of the invention administration of the compound or pharmaceutical composition of the present invention is commenced at lower dosage levels, with dosage levels being increased until the desired effect of preventing/treating the relevant medical indication, such as excess body weight or obesity, including morbid obesity, metabolic syndrome, type-2 diabetes, hypertension, atherosclerosis, arteriosclerosis and coronary heart diseases, is achieved. This would define a therapeutically effective amount. For the peptide of the present invention, alone or as part of a pharmaceutical composition, such doses may be between about 0.01 mg/kg and 100 mg/kg body weight, such as between about 0.01 mg/kg and 10 mg/kg body weight, for example between 10-100 µg/kg body weight.

For therapeutic use, the chosen glucagon analogue is formulated with a carrier that is pharmaceutically acceptable and is appropriate for delivering the peptide by the chosen route of administration. For the purpose of the present invention, peripheral parenteral routes include intravenous, intramuscular, subcutaneous, and intraperitoneal routes of administration. Certain compounds used in the present invention may also be amenable to administration by the oral, rectal, nasal, or lower respiratory routes. These are so-called non-parenteral routes. The present pharmaceutical composition comprises a glucagon analogue of the invention, or a salt or derivative thereof and a pharmaceutically acceptable carrier. Suitable pharmaceutically acceptable carriers are those used conventionally with peptide-based drugs, such as diluents, excipients and the like. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. Preferred buffer ranges are pH 4-8, pH 6.5-8, more preferably pH 7-7.5. Preservatives, such as para, meta, and ortho-cresol, methyl- and propylparaben, phenol, benzyl alcohol, sodium benzoate, benzoic acid, benzyl-benzoate, sorbic acid, propanoic acid, esters of p-hydroxybenzoic acid may be provided in the pharmaceutical composition. Stabilizers, preventing oxidation, deamidation, isomerisation, racemisation, cyclisation, peptide hydrolysis, such as e.g. ascorbic acid, methionine, tryptophane, EDTA, asparagine, lysine, arginine, glutamine and glycine may be provided in the pharmaceutical composition. Stabilizers, preventing aggregation, fibrillation and precipitation, such as Sodium dodecyl sulphate, polyethylene glycol, carboxymethyl cellulose, cyclodextrine may be provided in the pharmaceutical composition. Organic modifiers for solubilization or preventing aggregation, such as ethanol, acetic acid or acetate and salts thereof may be provided in the pharmaceutical composition. Isotonicity makers such as salts e.g. sodium chloride or most preferred carbohydrates e.g. dextrose, mannitol, lactose, trehalose, sucrose or mixtures thereof may be provided in the pharmaceutical composition.

Detergents, such as Tween 20, Tween 80, SDS, Poloxamers e.g. Pluronic F-68, Pluronic F-127, may be provided in the pharmaceutical composition. Dyes and even flavoring agents may be provided in the pharmaceutical composition. In another embodiment, a pharmaceutically acceptable acid addition salt of the glucagon peptide analogue is provided for. Suspending agents may be used.

Organic modifiers, such as ethanol, tertiary-buthanol, 2-propanol, ethanol, glycerol, Polyethylene glycol may be provided in the pharmaceutical formulation for lyophilization of a lyophilized product. Bulking agents and isotonicity makers such as salt e.g. sodium chloride, carbohydrates e.g. dextrose, mannitol, lactose, trehalose, sucrose or mixtures thereof, aminoacids e.g. glycine, glutamate, or excipients such as cystein, lecithin or human serum albumin, or mixtures thereof may be provided in the pharmaceutical composition for lyophilization.

The pharmaceutical compositions of the present invention may be formulated and used as tablets, capsules or elixirs for oral administration; suppositories for rectal administration; preferably sterile solutions or sterile powder or suspensions for injectable administration; and the like. The dose and method of administration can be tailored to achieve optimal efficacy but will depend on such factors as weight, diet, concurrent medication and other factors, which those skilled in the medical arts will recognize.

When administration is to be parenteral, such as intravenous and subcutaneous, e.g., on a daily basis, injectable pharmaceutical compositions can be prepared in conventional forms, either as aqueous solutions or suspensions; lyophilized, solid forms suitable for reconstitution immediately before use or suspension in liquid prior to injection, or as emulsions. It is envisaged that the administration regimen for the peptide of the invention should be peripheral subcutaneous or nasal. Diluents for reconstitution of the lyophilized product may be a suitable buffer from the list above, water, saline, dextrose, mannitol, lactose, trehalose, sucrose, lecithin, albumin, sodium glutamate, cysteine hydrochloride; or water for injection with addition of detergents, such as Tween 20, Tween 80, poloxamers e.g. pluronic F-68 or pluronic F-127, polyethylene glycol, and or with addition of preservatives such as para-, meta-, and ortho-cresol, methyl- and propylparaben, phenol, benzyl alcohol, sodium benzoate, benzoic acid, benzyl-benzoate, sorbic acid, propanoic acid, esters of p-hydroxybenzoic acid, and or with addition of an organic modifier such as ethanol, acitic acid, citric acid, lactic acid or salts thereof.

In addition, if desired, the injectable pharmaceutical compositions may contain minor amounts of non-toxic auxiliary substances, such as wetting agents, or pH buffering agents. Absorption enhancing preparations (e.g., liposomes, detergents and organic acids) may be utilized.

In one embodiment of the invention, the compounds are formulated for administration by infusion, e.g., when used as liquid nutritional supplements for patients on total parenteral nutrition therapy, or by injection, for example subcutaneously, intraperitoneal or intravenously, and are accordingly utilized as aqueous solutions in sterile and pyrogen-free form and optionally buffered to physiologically tolerable pH, e.g., a slightly acidic or physiological pH. Formulation for intramuscular administration may be based on solutions or suspensions in plant oil, e.g. canola oil, corn oil or soy bean oil. These oil based formulations may be stabilized by antioxidants e.g. BHA (butylated hydroxianisole) and BHT (butylated hydroxytoluene).

Thus, the present peptide compounds may be administered in a vehicle, such as distilled water or in saline, phosphate buffered saline, 5% dextrose solutions or oils. The solubility of the glucagon analogue may be enhanced, if desired, by incorporating a solubility enhancer, such as detergents and emulsifiers.

The aqueous carrier or vehicle can be supplemented for use as injectables with an amount of gelatin that serves to depot the glucagon analogue at or near the site of injection, for its slow release to the desired site of action. Alternative gelling agents, such as hyaluronic acid, may also be useful as depot agents.

The glucagon analogues of the invention may also be formulated as a slow release implantation device for extended and sustained administration of the glucagon peptide analogue. Such sustained release formulations may be in the form of a patch positioned externally on the body. Examples of sustained release formulations include composites of biocompatible polymers, such as poly(lactic acid), poly(lactic-co-glycolic acid), methylcellulose, hyaluronic acid, sialic acid, silicate, collagen, liposomes and the like. Sustained release formulations may be of particular interest when it is desirable to provide a high local concentration of a glucagon analogue of the invention.

The glucagon analogue may be utilized in the form of a sterile-filled vial or ampoule containing a pharmaceutically sufficient amount of the peptide, in either unit dose or multi-dose amounts. The vial or ampoule may contain the glucagon analogue and the desired carrier, as an administration ready formulation. Alternatively, the vial or ampoule may contain the glucagon peptide in a form, such as a lyophilized form, suitable for reconstitution in a suitable carrier, such as sterile water or phosphate-buffered saline.

As an alternative to injectable formulations, the glucagon analogue may be formulated for administration by other routes. Oral dosage forms, such as tablets, capsules and the like, can be formulated in accordance with standard pharmaceutical practice.

Nasal dosage forms can be formulated with addition of enhancers, such as Chitosan or detergents such as Tween 20, Tween 80, Poloxamers e.g. Pluronic F-68, Pluronic F-127; Brij 35, Brij 72, cremophor EL.

The therapeutic dosing and regimen most appropriate for patient treatment will of course vary with the disease or condition to be treated, and according to the patient's weight and other parameters. Without wishing to be bound by any particular theory, it is expected that doses, in the μg/kg range, and shorter or longer duration or frequency of treatment may produce therapeutically useful results.

In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage fora given subject. Such considerations are known to the skilled person.

A human dose of a glucagon peptide according to the invention may in one embodiment be from about 0.1 μg/kg body weight/day to about 10 mg/kg/day or 10 μg/kg body weight/day to about 10 mg/kg/day.

Medical Conditions

The peptides of the present invention are useful as a pharmaceutical agent for preventing increasing body weight or promoting loss of body weight. They are therefore useful for treating an individual suffering from excess body weight or obesity, including morbid obesity, metabolic syndrome, type-2 diabetes, hypertension, atherosclerosis, arteriosclerosis and coronary heart diseases.

Binding Assays

Membranes prepared from cells, which express either the hGlucagon-R or hGLP-1-R will be incubated with 30-100 μM [$^{125}$I]GLP-1, [$^{125}$I]glucagon in the absence or presence of increasing concentrations ($10^{-12}$-$10^{-6}$ M) of test peptides in 100 μl binding buffer (25 mM HEPES, 2.5 mM CaCl$_2$, 1 mM MgCl$_2$, & 0.1% BSA, pH 7.4). Non-specific binding will be defined at 1 μM Glucagon or GLP-1. The assay mixtures will be incubated for 30 min at 37° C. followed by rapid filtration on Unifilters (GF/C) that have been presoaked in 0.5% polyethylenimine for at least 120 min before use. The filters will be washed 3 times with buffer, dried for 90 min at 60° C., and counted in a TopCount scintillation counter in the presence of scintillation cocktail. IC50—values will be estimated by computer aided curve fitting.

Generation of Cell Lines Expressing Human Glucagon- and GLP-1 Receptors

The cDNA encoding either the human glucagon receptor (Glucagon-R) (primary accession number P47871) or the human glucagon-like peptide 1 receptor (GLP-1R) (primary accession number P43220) were cloned from the cDNA clones BC104854 (MGC:132514/IMAGE:8143857) or BC112126 (MGC:138331/IMAGE:8327594), respectively. The DNA encoding the Glucagon-R or the GLP-1-R was amplified by PCR using primers encoding terminal restriction sites for subcloning. The 5'-end primers additionally encoded a near Kozak consensus sequence to ensure efficient translation. The PCR products encoding the Glucagon-R or the GLP-1-R were subcloned into a mammalian expression vector. The fidelity of the DNA encoding the Glucagon-R and the GLP-1-R was confirmed by DNA sequencing. As the mammalian expression vector additionally encodes for G418 resistance, transfected cells may be selected by applying selection pressure with G418. Cells exhibiting G418 resistance will most likely also express the Glucagon-R or the GLP-1-R. The mammalian expression vectors encoding the Glucagon-R or the GLP-1-R were transfected into HEK293 cells by a standard calcium phosphate transfection method. 48 hr after transfection cells were seeded for limited dilution cloning and selected with 1 mg/ml G418 in the culture medium. Three weeks after 12 surviving colonies of Glucagon-R and GLP-1-R expressing cells were picked, propagated and tested in the Glucagon-R and GLP-1-R efficacy assays as described below. One Glucagon-R expressing clone and one GLP-1-R expressing clone were chosen for compound profiling.

Glucagon Receptor and GLP-1-Receptor Efficacy Assays

HEK293 cells expressing the hGlucagon-R, or hGLP-1-R are seeded at 40,000 cells per well in 96-well microtiter plates coated with 0.01% poly-L-lysine and grown for 1 day in culture in 100 μM growth medium. On the day of analysis, growth medium is removed and the cells washed once with 200 μl Tyrode buffer. Cells are incubated in 100 μl Tyrode buffer containing increasing concentrations of test peptides, 100 μM IBMX, and 6 mM glucose for up 15 min at 37° C. The reaction is stopped by addition of 25 μl 0.5 M HCl and incubated on ice for 60 min. The cAMP content is estimated using the FlashPlate® cAMP kit from Perkin-Elmer. EC$_{50}$ and relative efficacy are estimated by computer aided curve fitting.

We tested the peptide:

H-HSQGTFTSDYSKYLDRARADDFVAWLKST-NH$_2$ (Compound 3)

and obtained EC values: GluR: 7.3 μM (SD 1.9) and GLP1R: 9.3 μM (SD 1.5) giving a ratio of 1.27.

The corresponding values obtained for human glucagon were GluR: 0.0905 nM and GLP1R: 2.5 nM giving a EC50 [Glu]/EC50[GLP-1] ratio of 0.038.

The corresponding values obtained for human oxyntomodulin were GluR: 0.7759 nM and GLP1R: 2.400 nM (SD 1.5) giving a EC50[Glu]/EC50[GLP-1] ratio of 0.32

On re-testing of compound 3 the EC$_{50}$ values obtained were as follows: GluR: 0.49 nM and GLP-1R: 0.23 giving a EC50[Glu]/EC50[GLP-1] ratio of 2.13.

Effect of Glucagon/GLP-1 Co-Agonist on Food Intake and Body Weight in Diet Induced Obese (DIO) Mice Efficacious glucagon/GLP-1 receptor agonists are tested on 9-15 weeks old, 40 C57Bl/6J male mice which have been kept on a High Fat Diet (HFD)—60% high-fat food (Cat. No. D12492: 20% protein, 20% carbohydrate, and 60% fat, 5.2 kcal/g; Research Diets, New Jersey, USA, for 4 weeks. The high-fat food contains soybean oil (25/773.85 g) and lard (245/773.85 g).

DIO-mice are treated with vehicle or co-agonists for 2-4 weeks by bolus administration (s.c.) twice daily. Body weight is monitored daily throughout the experiment. At the end of the experimental period animals are sacrificed, blood collected for analysis of glycated hemoglobin and a range of hormones and peptides involved in regulation of appetite, food intake, body weight, and energy balances. In addition, the epididymal/perigonadal fat pads and retroperitoneal fat (WAT) as well as the intrascapular Brown Adipose Tissue (BAT) are dissected out and weighed.

EXAMPLES

Effect of Glucagon/GLP-1 Co-Agonist H-HSQGT-FTSDYSKYLDRARADDFVAWLKST-NH$_2$ (Compound 3) and Control Peptides Exendin-4 (Compound 1) and Oxyntomodulin (Compound 2) on Body Weight in Diet Induced Obese (D10) Mice Compound 3, Exendin-4 and oxyntomodulin were tested on 11-14 weeks old, 10 C57Bl/6J male mice which had been kept on a High Fat Diet (HFD)-60% high-fat food (Cat. No. D12492: 20% protein, 20% carbohydrate, and 60% fat, 5.2 kcal/g; Research Diets, New Jersey, USA, for 4 weeks. The high-fat food contained soybean oil (25 g/773.85 g) and lard (245 g/773.85 g). All peptides were manufactured according to solid phase peptide synthesis, e.g. as described in WO 98/11126 and WO 99/46283. The peptides used in the experiment have the following analytical data:

| Drug Name | MW (g/mol) | Peptide Content | Purity | Solvent |
|---|---|---|---|---|
| Exendin-4 (Compound 1) | 4187 | 88 | 98 | PBS |
| Oxyntomodulin (Compound 2) | 4450 | 83 | 91 | PBS |
| Compound 3 | 3365.7 | 83.1 | 90 | PBS |

Following an acclimatization treatment with 100 µl vehicle (PBS) once a day for two weeks DIO-mice were treated with vehicle, control peptides or Compound 3 for 4 weeks by bolus administration (s.c.) twice daily. Body weight was monitored daily throughout the experiment. At the end of the experimental period animals were sacrificed, blood collected for analysis of glycosylated hemoglobin and a range of hormones and peptides involved in regulation of appetite, food intake, body weight, and energy balances.

Prior to initiation of drug treatment the animals were randomized into groups of 10 animals each with similar average body weight (BW) and an eye blood sample (1 ml (EDTA)) were obtained from all animals (Week 10 of age). On week 7, 8, 9 and 10 (week 11, 12, 13 and 14 of age) the mice were treated twice daily s.c. with Exendin-4, oxyntomodulin, Compound 3 or vehicle. One group of animals was maintained on regular chow so as to serve as a non-obese/non-diabetic control group. To make the stress of handling the animals comparable to the other groups these animals were treated with PBS in the same regimen as the tested peptides. Throughout the study, body weights were obtained daily, which were used to calculate dose of the drugs. All solutions to be injected were adjusted to the same pH level (pH 6.5) in PBS. The daily injections took place between 8:00-8:30 a.m. and between 16:00-16:30 p.m. with fresh solutions prepared the same day. Prior to sacrifice, an eye blood sample (1 ml (EDTA)) was obtained. All animals were sacrificed at the end of the experiment by cervical dislocation under anesthesia (Hypnorm®-Dormicum®).

FIG. 1 is a column diagram showing body weight gain in high fat fed (D10) mice treated s.c. with vehicle, Exendin-4 amide (1-39) (Compound 1, H-HGEGTFTSDLSKQMEEE-AVRLFIEWLKNGGPSSGAPPPS-NH$_2$), oxyntomodulin (Compound 2, H-HSQGTFTSDYSKYLDSRRAQD-FVQWLMNTKRNRNNIA-OH) and the peptide Compound 3 for 28 days (animals eating chow are included for comparison). The figure shows that s.c. bolus administration of 500 nmol/kg twice daily of Compound 3 is able to reduce body weight gain comparable to oxyntomodulin treatment. (* p<0.05 compared to vehicle HFD (tukey post-hoc test)).

Figure 2:
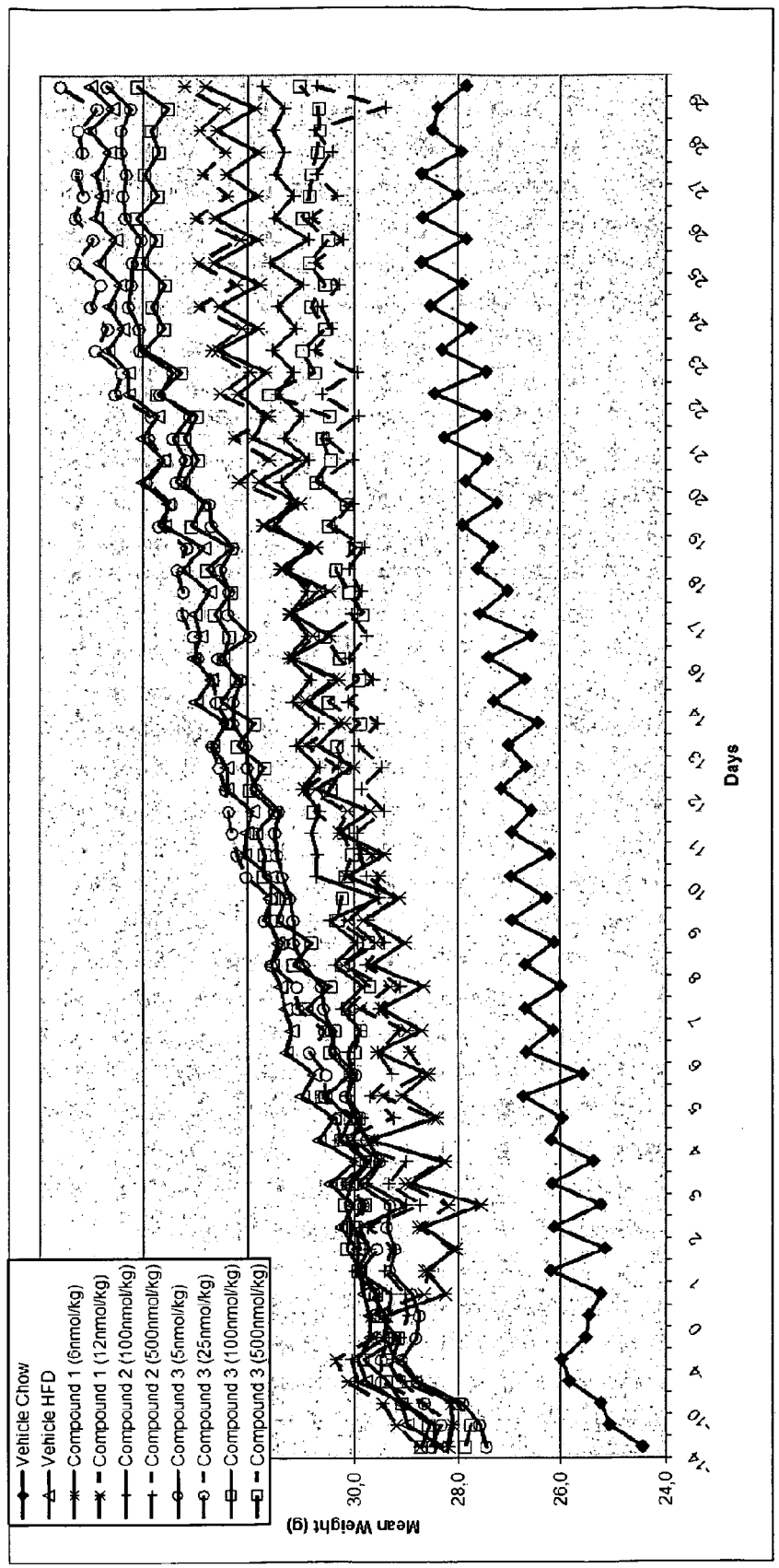
FIG. 2 shows that the weight-reducing effect of Compound 3 is sustained over time comparable to oxyntomodulin treatment and significantly different from exendin-4 treatment. Control peptides are the same as in FIG. 1.

FIG. 2 is a chart showing that the weight reducing effect of Compound 3 (same control peptides as in FIG. 1) is sustained over time comparable to oxyntomodulin treatment and significantly different from exendin-4 treatment.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

The invention claimed is:

1. A compound of the formula:

```
                                              (SEQ ID NO: 6)
R¹-Z¹-HSQGTFTSDYSKYLDRARADDFVAWLKST-Z²-R²
``` wherein:

R$^1$ is hydrogen, C$_{1-4}$ alkyl, methyl, acetyl, formyl, benzoyl or trifluoroacetyl;

R$^2$ is NH$_2$ or OH;

Z$^1$ and Z$^2$ are independently absent or a peptide sequence of 1-20 amino acids, wherein the amino acids are selected from the group consisting of Ala, Leu, Ser, Thr, Tyr, Asn, Gln, Asp, Glu, Lys, Arg, His, Met, Har, Dbu, Dpr and Orn;

or a pharmaceutically acceptable salt thereof.

2. A compound according to claim 1 of the formula:

```
R¹-HSQGTFTSDYSKYLDRARADDFVAWLKST-R²    (SEQ ID NO: 3)
``` wherein:

R$^1$ is hydrogen, C$_{1-4}$ alkyl, methyl, acetyl, formyl, benzoyl or trifluoroacetyl; R$^2$ is NH$_2$ or OH;

or a pharmaceutically acceptable salt thereof.

3. A compound according to claim 1 of the formula:

```
H-HSQGTFTSDYSKYLDRARADDFVAWLKST-NH₂    (SEQ ID NO: 3)
``` or a pharmaceutically acceptable salt thereof.

4. A nucleic acid encoding a compound according to claim 1.

5. An expression vector comprising a nucleic acid according to claim 4.

6. A host cell comprising a nucleic acid according to claim 4.

7. A pharmaceutical composition comprising a compound, according to claim 1, in admixture with pharmaceutically acceptable carrier.

8. A method of promoting weight loss, said method comprising administering a therapeutically effective amount of a compound according to claim 1 to a subject in need thereof.

* * * * *